United States Patent
Wu

(10) Patent No.: US 6,455,078 B1
(45) Date of Patent: Sep. 24, 2002

(54) MEDICINAL HERBAL COMPOSITION FOR TREATING LIVER DISEASES AND HIV

(76) Inventor: Tzu-Sheng Wu, No. 3, Lane 14, Jian-Gung 1$^{st}$ Road, Hsinchu, 300 (TW)

( * ) Notice: Subject to any disclaimer, the term of this patent is extended or adjusted under 35 U.S.C. 154(b) by 0 days.

(21) Appl. No.: 09/906,791

(22) Filed: Jul. 18, 2001

Related U.S. Application Data

(60) Provisional application No. 60/240,963, filed on Oct. 18, 2000.

(51) Int. Cl.$^7$ .................. A61K 35/78; A61K 35/37; A61K 35/38
(52) U.S. Cl. ................ 424/725; 424/728; 424/773; 424/777; 424/551; 514/893; 514/894
(58) Field of Search ................ 424/725, 728, 424/773, 777, 551; 514/893, 894

(56) References Cited

U.S. PATENT DOCUMENTS

| | | |
|---|---|---|
| 5,648,089 A | 7/1997 | Shawkat |
| 5,837,257 A | 11/1998 | Tsai et al. |
| 5,989,556 A | 11/1999 | Tsai et al. |

FOREIGN PATENT DOCUMENTS

| | | | |
|---|---|---|---|
| CN | 8800048 | * | 10/1988 |
| CN | 1148983 | * | 5/1997 |
| CN | 1151312 | * | 6/1997 |

* cited by examiner

*Primary Examiner*—Christopher R. Tate
(74) *Attorney, Agent, or Firm*—Fei-Fei Chao; Venable, Baetjer, Howard & Civiletti, LLP

(57) ABSTRACT

The present invention provides a herbal pharmaceutical composition for treating patients with liver diseases and/or HIV. The composition contains fifteen (15) ingredients, which are diffuse hedyotis, bistort rhizome, giant knotweed rhizome, Asiatic moonseed rhizome, baical skullcap root, bovine biliary powder, milkvetch root, barbary wolfberry fruit, sanqi, red ginseng, figwort root, Chinese magnoliavine fruit, turmeric root-tuber, hawthorn fruit, and Chinese angelica. Among the fifteen (15) ingredients, diffuse hedyotis, bistort rhizome, giant knotweed rhizome, and Chinese magnoliavine fruit are the required herbs which contribute to the efficacy of the pharmaceutical composition.

27 Claims, No Drawings

MEDICINAL HERBAL COMPOSITION FOR TREATING LIVER DISEASES AND HIV

CROSS-REFERNCE TO RELATED APPLICATION

The present application claims the benefit of the filing date of U.S. Provisional Application No. 60/240,963, filed on Oct. 18, 2000, which is herein incorporated by reference.

FIELD OF THE INVENTION

The present invention relates to a novel herbal pharmaceutical composition and its use for treating patients with liver diseases (e.g., viral hepatitis [such as Hepatitis A, Hepatitis B, Hepatitis C, Hepatitis D, and Hepatitis E], alcoholic or fatty liver, liver cirrhosis, and liver cancer) and HIV. The major ingredients in the herbal composition are diffuse hedyotis, bistort rhizome, giant knotweed rhizome, and Chinese magnoliavine fruit. The composition further contains Asiatic moonseed rhizome, baical skullcap root, bovine biliary powder, tumeric root-tuber, hawthorn fruit, sanqi, barbary wolfberry fruit, red ginseng, figwort root, Chinese angelica, and milkvetch root. The present invention also relates to a method for making the medicinal herbal composition and methods for treating patients with the medicinal herbal composition.

DESCRIPTION OF THE RELATED ART

Liver diseases have great impact on human health. Hepatitis is a kind of liver diseases, which is caused by liver inflammation due to infection of a variety of pathogens, which include, but are not limited to, viruses, bacteria, fungi, and protozoa. Hepatitis can be categorized as acute, chronic, or fulminant.

Viral hepatitis is an enterically transmitted liver disease due to viral infection. The major transmission means for viral hepatitis is through ingestion. Viral hepatitis can also be transmitted through blood transfusion or similar means of hepatitis-virus-carrying blood or blood product such as blood plasma. Viral hepatitis is widespread around the world. For example, there are approximately thirty million (30,000,000) viral hepatitis patients in China including an estimated number of nine million (9,000,000) new patients each year, and about one hundred million (100,000,000) hepatitis B virus (HBV) carriers. It is estimated that 10% of the pregnant women in China are HBV carriers. About one hundred thousand (100,000) people in China die of liver cancer originated as liver diseases each year.

Depending on the major etiologic agent, viral hepatitis is categorized into Hepatitis A, Hepatitis B, Hepatitis C, Hepatitis D, and Hepatitis E. Hepatitis A is caused by hepatitis A virus (HAV); Hepatitis A can affect anyone and occur in isolated cases as well as widespread epidemics. Hepatitis B is a serious disease caused by hepatitis B virus (HBV). HBV attacks the liver and can cause lifelong infection, cirrhosis (scarring) of the liver, liver cancer, liver failure, and death. Hepatitis C is caused by hepatitis C virus (HCV). Hepatitis D is caused by the hepatitis D virus (HDV) which is a defective single-stranded RNA virus that requires the helper function of HBV to replicate and to synthesize envelope protein composed of HBsAg to encapsulate HDV's genome. Hepatitis E is caused by hepatitis E virus (HEV), which is an etiologic agent of enterically transmitted non-A, non-B hepatitis. HEV is a spherical, non-enveloped, single-stranded RNA virus of approximately 32 to 34 nm in diameter. HEV has been provisionally classified in the Caliciviridae family; however, the organization of the HEV genome is substantially different from that of other Caliciviruses, and HEV may eventually be classified in a separate family.

The most common types of viral hepatitis are Hepatitis A, Hepatitis B, Hepatitis C, and Hepatitis E, which have similar major symptoms including decreased appetite, nausea, unease upper abdomen, lack of strength, etc. Acute jaundice is also one of the common symptoms. Chronic hepatitis is very difficult to cure. Severe hepatitis often comes on quickly and results in high mortality.

Traditional Chinese herbal compositions have been developed and shown success for preventing and treating various liver diseases. The types of traditional Chinese herbal medicine for treating hepatitis include medications having single or multiple herbal components and medications made of active ingredients extracted from the herbs.

For example, Qianglining injection solution is made of glycyrrhizic acid extracted from licorice (Glycyrrhiza). Glycyrrhizic acid reacts with ammonia to form a water-soluble ammonium salt of glycyrrhizic acid, which then can compound with amino acids. The injection solution is useful for treating chronic viral hepatitis, liver cirrhosis, and hepatoma. The total effective rate of qianglining injection solution is about 87.5%, in which 64.1% is significant, according to clinical studies conducted on hepatitis patients provided by Shanghai Huashan Hospital, Shanghai, China.

Yanhuanglian injection solution is derived from ground herb Yanhuanglian grown in Guangxi Province in China. The solution is useful for treating various types of hepatitis, liver cirrhosis, and liver cancer, with a reported clinical efficacy rate of 81.47%. The solution has an effective rate of 93.88% in cases involving acute jaundice patients, 87.50% in non-jaundice type hepatitis patients, 87.09% in chronic active type hepatitis patients, 69.23% in prolonged type hepatitis patients, and 80.95% in chronic cirrhosis patients. However, only 17.91% of the patients show changes of HBV surface antigen from positive to negative.

Shandougen (*Radix Sophorae Tonkinensis*) injection solution is useful for both acute and chronic viral hepatitis, and especially effective for chronic active hepatitis. As studied by Guangxi Medical College in Guangxi province, China, the total effective rate is 91.79% for chronic active hepatitis patients, and the substantial effective rate is 54.23%. Also, 64.93% of the patients' glutamate-pyruvate transaminase (GPT) level returns to normal in two (2) months after the treatment. However, some patients show recurring symptoms of hepatitis after the treatment is discontinued.

Umbellate pore fungus (*Polyporus umbellata*) injection solution has functions of improving immune function, inhibiting tumor, lowering level of transaminase, and inhibiting replication of hepatitis virus. After treating patients with chronic viral hepatitis with umbellate pore fungus injection solution, 35.6% of the patients return to normal serum GPT (SGPT) level, 76.61% of the patients show some lowering effects on transaminase level, 38.6% of the patients show HBV E antigen turning negative, and 13.1% of the patients show surface antigen turning negative.

Qidun fruit acid tablet has a total effective rate of 94.4% in patients with acute jaundice-type hepatitis. The total recovery rate is 64.8%. Qidun fruit acid tablet also shows an effective rate of 69.8% in chronic active hepatitis, in which 43.7% of the patients show a significant effect. The rate for HBsAg positive turning negative is 16.8%.

Gandezhi (Liver-curing) capsule has Wuren alcohol, *scutellarin*, mulberry fruit-spike (*Fructus Mori Albae*), salvia root (*Radix Salviae Miltiorrhizae*), and licorice (*Radix Glycyrrhizae Uralensis*) and is useful for lowering transaminase level. It has an effective rate of 80.0% for treating prolonged hepatitis and chronic hepatitis, according to studies reported by Guangzhou Zhongshan Medical College Hospital in China. There has been no report which shows that Gandzhi has effect on HBV Antigen turning negative.

Danggui (Chinese angelica root) pill is made of Chinese angelica root (*Radix Angelicae Sinensis*) and licorice (*Radix Glycyrrhizae Uralensis*). In a study conducted by Beijing Medical College in China, Danggui pill is effective for treating prolonged hepatitis (with an effective rate of 84.4%), chronic hepatitis (with an effective rate of 79.1%), and cirrhosis resulted from hepatitis (with an effective rate of 73.6%).

Hugang (liver-protecting) tablet is made from schisandra fruit (*Fructus Schisandrae Chinensis*) alcohol extractant, liver-protecting extractant (including Junchen, Zihu, and woad root (isatis root, *Radix Isatidis seu Baphicacanthi*)), and biliary powder, etc. It has an effective rate of 95.08% for treating chronic hepatitis (70% with significant effect), and 82.5% for treating cirrhosis (63% with significant effect).

Jigu ("chicken bone") grass pill is made of Jigu grass, billiary powder, and bovine bezoar (*Calculus Bovis*). As studied by Beijing Children's Hospital in China, Jigu grass pill has a total effective rate of 100% in patients with acute viral hepatitis, 73.3% in patients with chronic active hepatitis, 70.4% in patients with chronic prolonged type hepatitis. However, Jigu grass pill does not appear to have any effect on other types of prolonged hepatitis.

Wuzi ("five ester") capsule is made from schisandra fruit (*Fructus Schisandrae Chinensis*) alcohol extractant. It shows function of lowering GPT level and is useful for treating chronic prolonged hepatitis. The total effective rate of wuzi capsule is 95.33%, in which 74.21% is significant.

Ganfuneng (liver-healing) formula contains *astragalus* (*Radix astragali membranaceus*), hawthorn fruit (*Fructus crataegi*), pueraria (*Radix puerariae*), Cornu Bubali powder, San-qi, etc. It has an effective rate of 88.7% for chronic hepatitis patients and 79.1% for GPT recovery.

Biyansha Hepatitis B-curing formulation is made from diffuse hedyotis (*Hedyotis diffusa Willd.*), rubia root (*Radix Rubiae Cordifoliae*), Indigo Pulverata Levis, glabrous greenbrier rhizome (*Rhizoma Smilacis Glabrae*), salvia root (*Radix Salviae Miltiorrhizae*), finger citron fruit (*Fructus Citri Sarcodactylis*), hawthorn fruit (*Fructus Crataegi*), *Ganoderma Lucidum*, Ophiopogon tuber (*Tuber Ophiopogonis Japonici*), and silkworm feces (*Excrementum Bombycis Mori*). The formulation has been used for treating infectious HBV, acute and chronic hepatitis, early-stage cirrhosis, swollen liver and spleen, etc. It has a total effective rate of 84.75% and an HBsAg turning negative rate of 41.35%, as shown in the study of 314 HBV patients at Xian Medical University Second Affiliated Hospital in China.

Ganpikang ("liver-spleen" health) capsule contains fourteen (14) herbal components including bupleurum (*Radix Bupleuri*), San-qi, and bear gallbladder (*Vesica Fellea Ursi*) powder. It has a curing rate of 53.33% and an effective rate of 40.0 for chronic active HBV, and a curing rate of 63.33% and an effective rate of 26.67 for chronic prolonged HBV.

Ruanjianhugan ("liver-protecting") tablet contains sophora root (*Radix Sophorae Tonkinensis*), prunella (*Spica Prunellae Vulgaris*), bushy knotweed root and rhizome (*Radix et Rhizoma Polygoni Cuspidati*), scutellaria (*Radix Scutellariae Baicalensis*), salvia root (*Radix Salviae Miltiorrhizae*), astragalus (*Radix Astragali Membranaceus*), ligustrum (*Fructus Ligustri Lucidi*), cardamon (*Fructus Amomi*), and hawthorn fruit (*Fructus Crataegi*). It shows that 78% of the patients having HBeAg turned negative, 28–57% of the patients having HBsAg turned negative.

However, despite the effectiveness of the above herbal medicinal compositions in treating hepatitis, none of these compositions demonstrates significant effects on HBV antigen turning negative.

The present invention provides a novel pharmaceutical composition for treating liver diseases, particularly for treating patients with viral hepatitis (e.g., HAV, HBV, HCV and HEV), alcoholic or fatty liver, and liver cancer. The compositions described in the present invention also demonstrates significant clinical effects on patients with HIV. This composition is a natural Chinese medicine with little or no side effects and has no toxicity.

BRIEF SUMMARY OF THE INVENTION

The novel medicinal composition of the present invention comprises herb extracts from diffuse hedyotis, giant knotweed rhizome, bistort rhizome, Asiatic moonseed rhizome, baical skullcap root, bovine biliary powder, milkvetch root, barbary wolfberry fruit, sanqi, red ginseng, figwort root, Chinese magnoliavine fruit, turmeric root-tuber, hawthorn fruit, and Chinese angelica. The composition is effective in treating patients with liver diseases, including, but not limited to viral hepatitis (e.g., HAV, HBV, and HCV, and HEV), alcoholic or fatty liver, liver cirrhosis and liver cancer. It is also effective for treating patients with HIV.

Among the herbs used in the composition, diffuse hedyotis, bistort rhizome, giant knotweed rhizome, and Chinese magnoliavine fruit are the necessary ingredients that provide for the efficacy of the composition. Asiatic moonseed rhizome, baical skullcap root, bovine biliary powder, tumeric root-tuber, hawthorn fruit, and sanqi are used mainly to improve or enhance the flavour, toning, and medicinal effects of, and to balance the excessive effects cause by diffuse hedyotis, bistort rhizome, giant knotweed rhizome, and Chinese magnoliavine fruit. In addition, barbary wolfberry fruit, red ginseng, figwort root, Chinese angelica and milkvetch root can be added to the composition to provide further nutrition to the liver during the recovery stage.

The weight ratio of diffuse hedyotis, bistort rhizome, giant knotweed rhizome, and Chinese magnoliavine fruit is preferred to be about 3:3:1:2. The weight ratio of diffuse hedyotis, bistort rhizome, giant knotweed rhizome, Chinese magnoliavine fruit, asiatic moonseed rhizome, baical skullcap root, bovine biliary powder, tumeric root-tuber, hawthorn fruit, and sanqi is preferred to be about 3:3:1:2:1:1:0.1:1:2:1. The weight ratio of diffuse hedyotis, bistort rhizome, giant knotweed rhizome, Chinese magnoliavine fruit, asiatic moonseed rhizome, baical skullcap root, bovine biliary powder, tumeric root-tuber, hawthorn fruit, sanqi, barbary wolfberry fruit, red ginseng, figwort root, Chinese angelica, and milkvetch root is preferred to be about 3:3:1:2:1:1: 0.1:1:2:1:3:1:2:1:3.

The present invention also provides a method for preparing the herbal pharmaceutical composition, which comprises the steps of: (1) grinding and mixing the entire plant of diffuse hedyotis, the dried rhizome of bistort rhizome, the dried rhizome of giant knotweed rhizome, and the dried ripe fruit of Chinese magnoliavine fruit to form a herbal mixture; (2) boiling the herbal mixture in water in two times (first by boiling the mixture in water for 2 hours, then, after the mixture has cooled down, boiling the mixture again for 1.5 hours); (3) filtering the boiled herbal mixture to separate the herbs from the herbal solution; (4) concentrating the herbal solution (preferably concentrating from about 1.4 fold by volume to about 1 fold by volume); and (5) spray-drying and granulating the concentrated herbal solution into granules, which can be further encapsulated.

DETAILED DESCRIPTION OF THE INVENTION

Traditional Chinese medicine has been in existence for more than two thousand years. It has a proven record of success for curing many kinds of diseases. Traditional Chinese medicine utilizes a variety of herbs and natural substances. Each herb/natural substance has its unique characteristics. By combining and balancing the unique characteristics of herbs, a doctor can prescribe a formulation with enhanced medicinal activities and with less or no toxicity by synergizing the medicinal effects among various herbs, while in the meantime, cancelling out or neutralizing the toxic effects of the herbs. This, in Chinese herbal medicine, is regarded as to regulate between negative/hypoactive characteristics ("yin") and positive/hyperactive characteristics ("yang"), Under the definitions set forth in the traditional Chinese medicine, "yin" is defined as drugs which cure cold syndrome (which itself has hot or warm property), and "yang" is defined as drugs which cure heat syndrome (which itself has cold or cool property).

The pharmaceutical combination of the present invention comprises fifteen (15) ingredients, in which four (4) ingredients are the core ingredients which contribute to the primary efficacy and healing effect of the composition. They are: (1) diffuse hedyotis/spreading hedyotis (Pharmaceutical name: *Herba Hedyotidis diffusae*; Botanical name: *Hedyotis diffusa Willd.*); (2) bistort rhizome (Pharmaceutical name: *Rhizoma Bistortae*; Botanical name: *Polygonum bistorta L.*); (3) giant knotweed rhizome (Pharmaceutical name: *Rhizoma Polygoni Cuspidati*; Botanical name: *Polygonum cuspidatum Sieb. et Zucc.*), and (4) Chinese magnoliavine fruit (Pharmaceutical name: *Fructus Schisandrae* Chinensis; Botanical name: *Schisandra chinensis (Turcz.) Baill., S. sphenanthera Rehd. et Wils.*). The core ingredients are functioned in clearing heat and toxic substances while improving immune system and circulation, curing symptoms of jaundice, and having beneficial effect on internal organs.

There are six (6) additional ingredients that are used to improve and balance the pharmaceutical effects activities produced by the above named core ingredients. These six ingredients also have toning effect and can improve blood circulation in the liver. These six ingredients are: (1) Asiatic moonseed rhizome (Pharmaceutical name: *Rhizoma Menispermi*; Botanical name: *Menisermum dauricum DC*); (2) baical skullcap root (Pharmaceutical name: *Radix Scutellariae*; Botanical name: *Scutellaria baicalensis Georgi*); (3) bovine biliary powder (Zoological name: *Vesica Fellea Bovus*); (4) tumeric root-tuber (Pharmaceutical name: *Radix Curcumae*; Botanical name: *Curcuma wenyujin Y. H. Lee et Cl Ling*); (5) Hawthorn Fruit (Pharmaceutical name: *Fructus Crataegi;* Botanical name: *Crataegus pinnatifida Bge.*); and (6) sanqui (Pharmaceutical name: *Radix Notoginseng*; Botanical name: *Panax notoginseng (Burk.)*).

Finally, there are additional five (5) ingredients which are used to primarily provide nutrients and energy sources for patients so as to expedite the recovery process. These ingredients include: (1) barbary wolfberry fruit (Pharmaceutical name: *Fructus Lycii*; Botanical name: *Lycium barbarum L.*); (3) figwort root (Pharmaceutical name: *Radix Scrophulariae*; Botanical name: *Scrophularia ningpoensis*); (4) Chinese angelica (Pharmaceutical name: *Radix Angelicae sinensis*; Botanical name: *Angelica sinensis (Oliv.) Diels*); and (5) milkvetch root (Pharmaceutical name: *Radix Astragali*; Botanical name: *Astragalus membranaceus (Fisch.) Bge.*). Among these ingredients, red ginseng (*Radix Ginseng Rubra*) and milkvetch root (*Radix Astragali*) also have the capacity of improving immunological functions of the body to fense off diseases.

The pharmaceutical names, botanical or zoological names, family names, common descriptions, and major ingredients of the herbs used in the present invention is shown in Table 1.

TABLE 1

Herbs of the Present Pharmaceutical Composition

| Pharmaceutical Name | Botanical/ Zoological Name | Family | Common Description | Major Ingredients |
|---|---|---|---|---|
| Herba Hedyotidis Diffusae | *Heydyotis diffusa* (Willd.) Roxb., also known as *Oldenlandia diffusa* | Rubiaceae | heydyotis, oldenlandia | hentriacontane, stigmastatrienol, ursolic acid, oleanolic acid, β-sitosterol, ρ-coumaric, β-sitosterol-D-glucoside |
| Radix et Rhizoma Polygoni Cuspidati | *Polygonum cuspidatum* Sieb. et Zucc. | Polygonaceae | Giant Knotweed root and Rhizome | emodin, chrysophanol, rheic acid, emodin monomethyl ether, polygonim, and physcion-8-β-D-glucoside |
| Rhizoma Bistortae | *Polygonum bistorta* L. | Polygonaceae | Bistort Rhizome | n/a |
| Rhizoma Menispermi | *Menispermum dauricum* DC. | Menispermaceae | Asiatic Moonseed Rhizome | n/a |
| Radix Scutellariae Baicalensis | *Scutellaria baicalensis* Georgi | Labiatae | Baical Skullcap Root | baicalein, baicalin, wogonin, wogonoside, neobaicalein, oroxylin aglucuronide, camphesterol, β-sitosterol, benzoic acid |
| | Vesica Fellea Bovus | | Bovine Biliary powder | n/a |
| Radix Astragali | *Astragalus membranaceus* (Fisch.) Bge. var. mongholicus. (Bge.) Hsiao or *Astragalus membranaceus* (Fisch.) Bge. | Leguminosae | Milkvetch Root | D-β-asparagine, 2', 4'-dihydroxy-5,6-dimethoxyisoflavane, calycosin, formononetin,cycloastragenol,astragalosides, choline, betaine, kumatakenin, sucrose, glucoronic acid, β-sitosterol |
| Fructus Lycii | *Lycium barbarum* L. | Solanaceae | Barbary Wolfberry Fruit | betaine, carotene, physalien, thiamine, riboflavin, vitamin C, β-sitosterol, linoleic acid |

TABLE 1-continued

Herbs of the Present Pharmaceutical Composition

| Pharma-ceutical Name | Botanical/Zoological Name | Family | Common Description | Major Ingredients |
|---|---|---|---|---|
| Radix Noto-ginseng | Panax noto-ginseng (Burk.) F.H. chen, P. pseudoginseng Wall, P. sanchi Hoo. | Arali-aceae | San-chi, noto-ginseng, Tian qi, Shen san qi | Arasaponin A, arasaponin B, dencichine |
| Radix Ginseng Rubra | Panax Ginseng C. A. Mey | Arali-aceae | Red Ginseng | Panaxatriol, Panaxadiol, Other Panoxisides, Panoquilon, Panaxin, Ginsenin, α-Panaxin, Protopanaxadiol, Protopanaxtriol, Panacene, Panaxynol, Panaenic Acid, Panose, Dammarane, Glucose, Fructose, Maltose, Sucrose, Nicrotinic Acid, Riboflavin, Thiamine |
| Radix Scrophu-lariae Ning-poensis | Scrophularia ning-poensis Hemsl. or S. buer-geriana Miq. | Scrophu-lariaceae | Figwort Root, Scrophu-laria | l-asparagine, oleic acid, linoleic acid, stearic acid, carotene |
| Fructus Schis-andrae Chinensis | Schisandra chinensis (Turcz.) Baill., S. sphenanthera Rehd. et Wils. | Magno-liaceae | Chinese Magnolia-vine Fruit, schisandra fruit | sesquicarene, β-bisabolene, β-chamigrene, α-ylangene, schizandrin, pseudo-γ-schizandrin, deoxyschizandrin, schizandrol, citral, stigmasterol, vitamin C, vitamin E |
| Tuber Curcumae | Curcuma wenyujin Y. H. Lee et C. Ling., or Curcuma Longa L., or Curcuma aromatica Salisb., or Curcuma zedoaria Rosc., or Curcuma kwangsiensis S. G.Lee et C. F. Liang | Zingi-beraceae | Turmeric Root-tuber, curcuma | d-camphene, d-camphor, 1-α-curcumene, 1-β-curcumene, curcumin, demethoxycurcumin, bisdemethoxycurcumin, turmerone,ar-turmerone, carvone, ρ-tolylmethylcarbinoldiferuloyl-methane |
| Fructus Crataegi | Crataegus pinnatifida Bge.; C. pinnatifida Bge. var. major N.E. Br. or C. suneata Sieb. et Zucc. | Rosaceae | Hawthorn Fruit | crategolic acid, citric acid, tartaric acid, flavone, sugars, glycosides, vitamin C |
| Radix Angelicae Sinensis | Angelica sinensis (Oliv.) Diels | Umbel-liferae | Chinese Angelica root, tang-kuei | butylidene phthalide, ligustilide, n-butylidene-phthalide, sequiterpenes, carvacrol, dihydrophthalic anhydride, sucrose, vitamin $B_{12}$, carotene, β-sitosterol |

Diffuse hedyotis or spreading hedyotis (*Herba Hedyotidis Diffusae*) belongs to the family of Rubiaceae. The entire plant is used as an herbal medicinal component. The herb has no toxicity. The herb is harvested in summer and autumn in mainland China and in late spring or early winter in Taiwan. In "Materia Medica" (Chinese Herbal medicine), compiled and translated by Dan Bensky & Andrew Gamble, diffuse hedyotidis clears heat and resolves dampness by promoting urination. It is particularly useful for relieving hot painful urinary dysfunction and damp-heat jaundice. Diffuse hedyotidis is the major ingredient in the present herbal pharmaceutical composition which contributes to the medicinal effect on liver diseases and HIV.

Bistort rhizome (*Rhizoma Bistortae*) is the dried rhizome of the plant *Polygonum bistorta L*. It belongs to the family of Polygonaceae. Bistort rhizome has moderate cool property (meaning that bistor rhizome is an "yang" herb). It can be used to remove toxic heat, to promote the subsidence of swelling and to stop bleeding.

Giant knotweed rhizome (*Radix et Rhizoma Polygoni Cuspidati*) is the dried rhizome and root of *polygonum cuspidatum Sieb. et Zucc*. It belongs to the family of Polygonaceae. The plant is grown throughout China, especially Jiangsu, Zhejiang, Anhui, Guangdong, Guangxi, Sichuan, and Guizhou provinces. The plant is harvested in spring and autumn. Giant knotweed rhizome is normally used to dispel damp, to eliminate blood stasis and alleviate pain, to relieve cough, and to resolve phlegm.

Chinese magnoliavine fruit (*Fructus Schisandrae*) is the dried ripe fruit of *Schisandra chinensis (Turcz.) Baill.* or *Schisandra sphenanthera Rehd. et Wils.* It belongs to the family of Magnoliaceae. The former, the best of its kind, is produced in northern parts of China and is habitually called "Northern schisandra fruit"; the latter is commonly referred to as the "Southern schisandra fruit" as it is produced in the southern parts of China. Both kinds can be used for the pharmaceutical preparation of the present invention. The fruit is collected in autumn and dried under the sun after removing the fruit stalks. Chinese magnoliavine fruit is generally used to arrest discharges, replenish qi, promote fluid secretion, tonify the kidney, and induce sedation. Chinese magnoliavine fruit can also decrease the level of GPT (glutamate-pyruvate transaminase) in patients with hepatitis.

Asiatic moonseed rhizome (*Rhizoma Menispermi*) is the dried rhizome of *Menispermum dauricum DC*. It belongs to the family of Menispermaceae. Asiatic moonseed rhizome has cool property. It can be used to remove toxic heat and relieve rheumatic pains.

Baical skullcap root (*Radix Scutellariae*) is the dried root of *Scutellaria baicalensis georgi*. It belongs to the family of Labiatae. The plant is produced in the provinces of Hebei, Shanxi, Inner Mongolia, etc., and collected in spring or autumn. Baical skullcap root is used to remove damp-heat, counteract toxicity, arrest bleeding, and prevent abortion, in patients.

Bovine biliary powder is the gallbladder of the cow, *Vesica Fellea Bovus*. It can clear heat and alleviate spasms.

Turmeric root-tuber (*Radix Curcumae*) is the dried root tuber of *Curcuma wenyujin* Y. H. Lee et C. Ling., or *Curcuma Longa L.*, or *Curcuma aromatica Salisb.*, or *Curcuma zedoaria Rosc.*, or *Curcuma kwangsiensis* S. G. Lee et C. F. Liang. The herb is mainly produced in Sichuan, Zhejiang, Guangdong, and Guangxi provinces in China, and harvested in winter or spring, washed clean after the removal of the hairy rootlets, boiled thoroughly, and dried in the sun. It belongs to the family of Zingiberaceae. Turmeric root-tuber tastes bitter and had cool property. It can be used to clear heat, alleviate spasms and chest pain, and resolve phlegm.

Hawthorn fruit (*Fructus Crataegi*) is the dried ripe fruit of *Crataegus pinnatifida Bge.* var *major N. E. Br.*, or *Crataegus pinnatifida Bge.*, or *Crataegus cuneata Sieb*. It is produced primarily in Henan, Jiangsu, and Shandong provinces of China. It is harvested in autumn, sliced, and dried in sunlight. It belongs to the family of Rosaceae. Hawthorn fruit is normally used to stimulate digestion and promote the functional activity of the stomach. It can also improve the normal blood flow and dissipate blood stasis.

Sanqi, or San-chi, (*Radix Notoginseng*) belong to the family of Araliaceae. Sanchi (Sanqi) is the dried root of *Panax notoginseng* (*Burk.*) *F. H. Chen*. The plant is also known as *P. pseudoginseng Wall* and *P. sanchi Hoo*. The plant grows in Yunnan, Guangxi, Sichuan, Guizhou, and Jiangxi provinces of China, and is harvested in the autumn or winter of the third or seventh year, either before the flowers bloom (better) or after the fruit is ripe. H. Gao et al., *Pharmaceutical Research*, (1996) 13(8): 1196–1200, disclose that polysaccharides from *Panax notoginseng* (San-Chi) have immuno-stimulating activities in vitro.

Barbary wolfberry fruit (*Fructus Lycii*) is the dried ripe fruit of *Lycium barbarum L.* It belongs to the family of Solanaceae. The plant is mainly produced in Ningxia, Gansu, and Qinghai provinces of China. It is harvested in summer and autumn. It nourishes and tonifies the liver and kidneys. It can also replenish vital essence and improve eyesight.

Figwort Root (*Radix Scrophulariae*) is the dried root of *Scrophularia ningpoensis Hemsl*. It belongs to the family of Scrophulariaceae. The herb is chiefly produced in Zhejiang and Sichuan provinces of China and harvested in winter when the part of the plant above-ground has withered. The roots are piled and dried in sunlight alternately until the inside becomes black and then sliced for use. Figwort root can reduce heat from blood. It als has nourishing capacity and can counteract toxicity.

Red ginseng (*Radix Ginseng Rubra*) is the steamed and dried root of the cultivated form of *Panax ginseng C. A. Mey* (commonly known as "Yuanshen"). The herb turns red after being steamed and its properties become warmer in nature. It belongs to the family of Araliaceae. The pharmaceutical effects of ginseng is in its dried root. Ginseng has effects on central nervous system. It enhances both stimulatory and inhibitory processes in the central nervous system, thereby improving the adaptability of nervous responses. Ginseng can also lower serum glucose and cholesterol. It also shows therapeutic and preventive effect on peptic ulcer.

Chinese angelica (*Radix Angelicae Sinensis*) is the dried root of *Angelica sinensis* (*Oliv.*) *Diels*. It belongs to the family of Umbelliferae. The herb is mainly produced in Gansu and Shanxi provinces of China. It is harvested in late autumn, smoked dry on slow fire after getting rid of the rootlets, sliced, or stir-baked with wine. Chinese angelica can enrich blood, promote blood circulation, regulate menstruation, relieve pain, and relax bowels.

Milkvetch root (*Radix Astragali*) is the dried root of *Astragalus membranaceus* (*Fisch.*) *Bge.* var. *mongholicus.* (*Bge.*) *Hsiao* or *Astragalus membranaceus* (*Fisch.*) *Bge*. It belongs to the family of Leguminosae. The herb is mainly produced in Shanxi, Gansu, Heilongjiang, and Inner Mongolia of China. The plant of four-year old or older is harvested in spring or autumn. Milkvetch root can promote discharge of pus and the growth of new tissue.

The herbal composition of the present invention was suitable for preparation in a scale typical for pharmaceutical industry as well as for smaller measure.

In the process for making the herbal composition of the present invention, the individual herbal components are pretreated according to the common procedures. The herbs are cut and put in a container with water to boil and simmer twice. The first time of simmering takes two hours, the solution is collected, and water is added for the second time of simmering for 1.5 hour. The solutions from the simmering steps are collected by passing through a sieve/filter. The filtrate is then condensed from about 1.4 fold by volume to 1.0 fold by volume. Subsequently, the liquid condensate is spray-dried and granulated to form particles. The particles are further packaged and preserved for use or for further analysis by the conventional means of the active ingredients to ensure their quality.

The composition of the present invention can further be processed and formulated in a form suitable for oral administration or intravenous injection.

The following example is illustrative, but not limiting the scope of the present invention. Reasonable variations, such as those occur to reasonable artisan, can be made herein without departing from the scope of the present invention.

EXAMPLE 1

Pharmaceutical Preparation

The kinds and amounts of herbal ingredients used in the process of making the pharmaceutical composition of the present invention are described in Table 2.

TABLE 2

Ingredients Used In Example 1.

| Component | Amount (g) | Component | Amount (g) |
|---|---|---|---|
| Diffuse heydyotis | 90 | Sanchi | 30 |
| Bistort Rhizome | 90 | Red Ginseng | 30 |
| Giant Knotweed root and Rhizome | 30 | Figwort root | 60 |
| Asiatic Moonseed Rhizome | 30 | Chinese Magnoliavine Fruit | 60 |
| Baical Skullcap Root | 30 | Turmeric Root-tuber | 30 |
| Bovine Biliary powder | 3 | Hawthorn fruit | 60 |
| Milkvetch Root | 60 | Chinese Angelica | 30 |
| Barbary Wolfberry Fruit | 90 | | |

The individual herbal components are pretreated according to common procedures. The herbs are weighed according to Table 2. The herbs are cut into small pieces and put in a container with water to boil and simmer twice, the first time for two hours, and the second for 1.5 hour. After the first simmering, solution is poured out and water is added to the container for the second simmering. The solutions from the two simmering steps are collected to pass through a sieve/filter, and then, condensed at a ratio of 1:1.4. The liquid condensate is spray-dried and granulated to form particles. The particles were further packaged into about 1000 capsules. The capsules are called "Yigan Kang capsules", abbreviated "YGK" capsules. The liquid condensate can also be made for intravenous injection. The injection solution is called "YGK" herbal injection solution. The herbal composition of the present invention is called "YGK" herbal composition.

EXAMPLE 2

Efficacy of the YGK Herbal Composition on Treatment of Patients with Hepatitis B (HBV)

The clinical research was conducted in the Liberty Military Hospital 211 in China. The course of hepatitis B is determined by many factors, including immune response, host genetic factors, and HBV mutations. The chronic hepatitis distinguishes from the acute hepatitis. The acute hepatitis is the active and symptomatic infection of the liver. A patient with the acute hepatitis is contagious. Symptoms of acute HBV infection are non-specific, but may include malaise, anorexia or jaundice. A chronic hepatitis patient is asymptomatic. The HBV is present in the liver and blood, although there are usually no obvious physical symptoms. Specific blood tests will reveal the presence of the virus, and the patient is also contagious via blood, birth, sex, needles, etc. Cirrhosis is the pathological dysfunctional state of the liver, the hardening of the liver as the result of chronic hepatitis, chronic persistent hepatitis (CPH) and chronic active hepatitis (CAH).

A total of 948 patients with acute HBV, chronic HBV, and liver cirrhosis participated in a clinical comparative study. The patients were divided into two (2) groups. The study group had 642 patients and the comparative group has 306 patients. The data on patients who participated in this study are listed in Table 3.

TABLE 3

Patients Data in the Clinical Study

| Group | Study Group | Comparative Group |
|---|---|---|
| Total Number of Patients | 642 | 306 |
| Sex Distribution of the Patients | Male: 482<br>Female: 160 | Male: 229<br>Female: 77 |
| Age Distribution of Patients | 7 to 74 years old<br>(average age: 32.5) | 8 to 70 years old<br>(average age: 30.5) |
| *Symptoms of Patients' Liver Disease | Acute Hepatitis B: 282<br>Chronic Hepatitis: 276<br>Cirrhosis: 84 | Acute Hepatitis B: 109<br>Chronic Hepatitis B: 114<br>Cirrhosis: 83 |

*According to the diagnosis criteria of Hepatitis revised at the Shanghai Hepatitis Conference in 1980, Shanghai, China.)

The patients were treated according to the following regime:

(1) The patients in the study group were each orally administered eight (8) YCK herbal composition containing the herbal composition of the present invention per day.

(2) The patients in the comparative group were each orally administered four (4) Hugang ("liver protecting") tablets per day. A description of Hugang tablets has been provided in the "Background" section, supra.

The treatment lasts for ninety (90) days.

Table 4 shows the results of this clinical comparative study.

TABLE 4

Effects of YGK Capsule Treatment

| Group | Number of Patients with Positive Effect* (%) |
|---|---|
| Study (642 patients) | 456 (71.03%) |
| Comparative (306 patients) | 104 (33.98%) |

($p < 0.01$)
*Positive effect means that the hepatitis B envelope antigen (HBeAg) and HBV DNA of the patients turn negative after taking the YGK herbal composition for 90 days.

As indicated in Table 4, approximately 71.03% of patients who took the YGK herbal composition for 90 days show positive responses to the herbal composition. This is contrary to the comparative group where the patients were given a popular "liver protecting" tablets which were available in the Chinese market. Patients who had taken the "liver protecting" tablets only have an effective rate of approximately 33.98% to show improvement in their liver diseases.

The Hepatitis B virus (HBV) consists of a surface and a core. The core contains a DNA polymerase and an e antigen. The DNA structure is double stranded and circular. HBV has four (4) genes encoding four (4) polypeptides: the S (surface), the C (core), the P (polymerase), and the X (transcriptional transactivating).

The S gene consists of three (3) regions, the pre-S 1 region, the pre-S2 region, and the region that encodes the surface protein (HBsAg). Very rarely a mutation occurs in the S gene which aborts the production of HBsAg so that a person maybe HBsAg negative but still has the virus present as determined by HBV DNA. In addition, the HBsAg particles are antigenically complex and the antigenic determinants have been identified as one single common determinant designated a, and four (4) major subdeterminants designated as d, y, w, and r. Thus, the four (4) major determinants are adw, adr, ayw, and ayr.

The C gene consists of two (2) regions, the pre-core region and the core region, which encodes for two different proteins, the core antigen (HBcAg), and the e antigen (HBeAg). A mutation in the pre-core region may stop the production of HBeAg, thus, a person maybe HBeAg negative, but HBsAg positive and HBV DNA positive. Another type of mutant in the core region is called HBV2. The patients that have HBV2 mutant are HBsAg positive but lack HBeAg and HBV DNA.

Because of the complexity and the antigenic differences among the virus, there are a number of tests available for HBV including:

(1) a test for HBsAg, which is an indicator of the presence of the HBV;

(2) a test for HBeAg, which correlates with the viral replication and infectivity, it indicates a high amount of the virus in the blood, thus, is an indicator of the activity and infectivity of the HBV; and (3) a test for HBV DNA, which is an indication of the virus presence and activity.

Tables 5–7 indicated the change of Hepatitis B envelope Antigen ("HBeAg"), Hepatitis B surface antigen ("HBsAg"), heptomegaly, and splenomegaly in the patients after the treatment.

TABLE 5

Effect of Herbal Composition on HBeAg in Patients

| Group | Study Group | Comparative Group |
|---|---|---|
| Acute Hepatitis Patients | | |
| Number of Patients with HbeAg(+) | 260 | 78 |
| Number of Patients with HbeAg(+) After Treatment | 48 | 59 |
| Percentage of Patients With HbeAg Turning Negative | 81.5% | 24.36% |
| Chronic Hepatitis Patients | | |
| Number of HbeAg(+) Patients | 206 | 82 |
| Number of HbeAg(+) Patients After Treatment | 74 | 64 |
| Percentage of Patients With HbeAg Turning Negative | 64.0% | 21.95% |
| Cirrhosis Patients | | |
| Number of HbeAg(+) Patients | 24 | 26 |
| Number of HbeAg(+) Patients After Treatment | 14 | 22 |
| Percentage of Patients With HbeAg Turning Negative | 41.7% | 15.38% |

As indicated in Table 5, the percentages of patients with HBeAg turning negative in all three (3) categories of patients (including acute hepatitis, chronic hepatitis, and cirrhosis) are 2.7–3.3 times higher than those of the comparative groups. This demonstrates that the YGK herbal composition had significant effect on HBeAg turning negative and inhibiting HBV activity and infectivity.

TABLE 6

Effect of Herbal Composition on HBsAg in Patients

| Group | Study Group | Control Group |
|---|---|---|
| Acute Hepatitus Patients | | |
| Number of Patients with HBsAg(+) | 262 | 84 |
| Number of Patients with HBsAg(+) After Treatment | 116 | 73 |
| Percentage of Patients With HBsAg Turning Negative | 55.7% | 13.09% |
| Chronic Hepatitis Patients | | |
| Number of HBsAg(+) Patients | 216 | 87 |
| Number of HBsAg(+) Patients After Treatment | 118 | 78 |
| Percentage of Patients With HBsAg Turning Negative | 45.37% | 10.30% |
| Cirrhosis Patients | | |
| Number of HBsAg(+) Patients | 64 | 43 |
| Number of HBsAg(+) Patients After Treatrnent | 50 | 40 |
| Percentage of Patients With HBsAg Turning Negative | 21.88% | 6.98% |

As indicated in Table 6, the percentages of patients with HBsAg turning negative in all three (3) categories of patients including acute hepatitis, chronic hepatitis, and cirrhosis were 3.1–4.4 times of those of the comparative groups. This demonstrates that the YGK herbal composition had significant effect on HBsAg turning negative and inhibiting the HBV.

In addition to HBeAg and HBsAg turning negative, the YGK herbal composition also show greater effects on increased appetite and decreased various symptoms of liver diseases than the comparative group using Hugang "liver protecting" tablets.

TABLE 7

Effect on Hepato-Splenmegaly

| Group | Reduced Hepatomegaly | Reduced Splenomegaly |
|---|---|---|
| Study Group | 79.72% | 58.54% |
| Comparative Group | 30% | 28.8% |

Heptomegaly and splenomegaly are related to and possibly caused by viral infection. The reduced hepatomegaly and splenomegaly in patients was indicative to reduced symptoms of viral infection.

In summary, the YKG herbal composition demonstrates effect on treating patients with HBV, which including acute hepatitis B, chronic hepatitis B, and cirrhosis.

EXAMPLE 3

Effects of the YGK Herbal Composition on Treatement of Patients with Chronic Hepatitis B (HBV)

The clinical research was conducted in the Liberty Military 302 Hospital, Ninth Section, China. The research was conducted on treatment effects of the herbal composition of the present invention on chronic hepatitis B patients.

Chronic Hepatitis is an ongoing injury to the cells of the liver with inflammation which lasts for longer than six months. The causes of chronic hepatitis include: viruses, metabolic or immunologic abnormalities and medications. Symptoms resulted from the injury of hepatocytes, the inflammation or from the resulting scarring is called cirrhosis. Chronic hepatitis may follow acute hepatitis B or C or may develop quietly without an acute illness. Liver biopsy is helpful in that it confirms the diagnosis, aids in establishing the cause (etiology) and can demonstrate the presence of cirrhosis. It is less helpful in judging the response to treatment. Approximately 25% patients with chronic hepatitis B will develop cirrhosis, causing permanent and serious liver damage. Chronic carriers of HBV are far more likely to develop hepatocellular carcinoma than non-carriers.

It is believed that chronic infections develop as the result of a weak T helper (Th) cell response to the virus, in particular to the HBsAg. The T cell response is responsible for clearing the infected cells in the host's system. When the clearance is inefficient and the infected cells persist in the body, a chronic infection develops. As the HBsAg titer Table 9 shows the changes in HBsAg, HBeAg, and HBV-DNA in patients after treatment with the YGK herbal composition (the study group) or Hugang tablets (the comparative group).

As indicated above, HBsAg can be detected in patients with acute infection as well as patients who are chronic HBV carriers. In the serological test, decreased titer of HBsAg indicates that the symptoms of HBV are lessened and the patient is approaching the immune state.

TABLE 9

The Changes of HBsAg, HBeAg, and HBV-DNA in Patients

| Group | HBsAg | | HbeAg | | HBV-DNA Sero-Negative | SGPT Recovery Rate (%) |
| --- | --- | --- | --- | --- | --- | --- |
| | Sero-Negative (%) | Decreased Titer (%) | Sero-Negative (%) | Decreased Titer (%) | | |
| Study Group | 1/30 (3.33%) | 6/30 (20.00%) | 12/26 (46.15%) | 6/26 (23.08%) | 9/15 (60.00%) | 73.33% |
| Comparative Group | 0/30 (0%) | 2/30 (6.67%) | 5/27 (18.52%) | 2/27 (7.41%) | 4/18 (22.22%) | 71.43% |

$p < 0.05$.

increases, the patient moves into acute, symptomatic disease. When the titer of anti-HBsAg rises, the symptoms of HBV begin to decline and patient reaches the immune state.

Chronic hepatitis has been divided into two categories based on histologic findings: chronic persistent hepatitis (CPH) and chronic active hepatitis (CAH). Characteristically, specimens from liver biopsy identified as CPH show inflammation confined to the portal triad (does not penetrate the limiting plate). Specimens identified as CAH show inflammation that penetrates the limiting plate, extending to the surrounding individual hepatocyte and yielding piecemeal necrosis. Under this schema, CAH eventually reaches a point where lobular architecture is destroyed, and bands of necrosis (bridging necrosis) are replaced by scar tissue (bridging fibrosis), resulting in the characteristic features of cirrhosis.

Sixty (60) patients with chronic hepatitis B are divided into two (2) groups, one group for treatment with YKG herbal composition and the other with Hugang ("Liver protecting") tablets. The study was conducted and maintained for three (3) months. The patients information in the two (2) groups are shown in Table 8:

TABLE 8

Compositions of the Patients in the Clinical Study

| Group | Study Group | Comparative Group |
| --- | --- | --- |
| Total Number of Patients | 30 | 30 |
| Sex Distribution of the Patients | Male: 26 Female: 4 | Male: 25 Female: 5 |
| Age Average Patients | 32.8 | 35.1 |
| Duration of Illness | 2 months to 11 years | 2 months to 9 years |
| *Symptoms of Patients' Liver Disease | CPH: 13 CAH: 17 | CPH: 10 CAH: 20 |

*According to the diagnosis criteria of hepatitis revised at the Shanghai Hepatitis Conference in 1980.

As indicated in Table 9, the YGK herbal composition has significant effects on chronic hepatitis patients. Patients treated with the YGK herbal composition have Serum Glutamic Pyruvic Transaminase (SGPT/ALT) recovery rate of 73.33%, HBeAg turning negative rate of 46.15%, HBV-DNA turning negative rate of 60.00%, suggesting that the YGK herbal composition has significant effects on inhibition of HBV replication and presence and depletion of aminotransferase. In addition, there was no toxic adverse reaction on the patients treated with the YGK herbal composition, accodring to clinical obervation.

EXAMPLE 4

Case Studies on Effects of the YGK Herbal Composition on Patients with Hepatitis B The clinical research was conducted in the Contagious Disease Department of People's Liberation Army Hospital Branch 113 in China. The research was conducted on treatment effects of the YGK herbal composition on hepatitis B patients.

Each patient was tested for various markers. Serum alanine aminotransferase (ALT) is an enzyme appears in liver cells, with lesser amounts in the kidneys, heart, and skeletal muscles. When such damage occurs, ALT is released from the liver cells into the bloodstream, often before jaundice appears, resulting in abnormally high serum level of ALT that last for days or weeks. ALT is a relatively specific indicator of acute liver cell damage. Serum bilirubin (BIL) is also tested as an indication of liver diseases.

Case #1 was a twenty-four years old male patient with chronic hepatitis B, with general weakness for more than one year. Table 10 shows the diagnoses of patient case #1 before and after treatment with the YGK herbal composition:

TABLE 10

Diagnoses of the Patient #1 Before and After the Treatment

| | TBIL (nmol/L) | ALT (U/L) | HBSAg | HbsAb | HBeAg | HbeAb | HbcAg | HBcAb (IgM) | PCR HBV-DNA |
|---|---|---|---|---|---|---|---|---|---|
| Before Treatment | 42 | 231 | + (1:64) | − | + | − | + | + | ++ |
| After Treatment | 18.6 | 66 | − | + | − | + | + | + | −− |

Table 10 indicates that the patient was in a state of immunity towards HBV and with alleviated infection as shown by the significant decrease of the viral DNA, and viral proteins, HBsAg, HBeAg, HBcAg, with increased amount of the antibodies against the viral protein in the serum.

Case #2 was a sixty-six years old male patient with recurrent abdominal fullness and general weakness for about ten (10) years with liver cirrhosis and splenomegaly. The following are the diagnoses of the patient before and after treatment with the YGK herbal composition (Table 11).

TABLE 11

Diagnoses of the Patient #2 Before and After Treatment with the YGK herbal composition

| | TBIL (nmol/L) | ALT (U/L) | HBsAg | HbsAb | HBeAg | HbeAb | HbcAg | HBcAb (IgM) | PCR HBV-DNA |
|---|---|---|---|---|---|---|---|---|---|
| Before Treatment | 44.8 | 382 | + (1:64) | − | + | − | + | + | +++ |
| After Treatment | 25.3 | 43.8 | + (1:32) | − | − | + | + | − | + |

Table 11 shows that patient #2 was in a state of alleviated infection symptoms towards HBV as shown by the significant decrease of viral DNA, and viral proteins., The data also show an increase in immunity as evidenced by reduced amount of HBsAg, HBeAg, HBcAg, and an increased amount of the antibodies against the viral proteins in the serum.

Case #3 was a thirty-one years old male patient with general weakness for more than one (1) month, treated in local Chinese Medicine clinic and subsequently hospitalized as acute biliary hepatitis B patient. The following are the diagnoses of the patient before and after treatment with the YGK herbal composition (Table 12).

Table 12 shows that the patient was in a state of alleviated infection symptoms towards HBV as shown by the significant decrease of viral DNA, and viral proteins. The data also show an increase in immunity as evidenced by reduced amount of HBsAg, HBeAg, HBcAg, and an increased amount of the antibodies against the viral proteins in the serum.

Case #4 was a forty-five years old male acute biliary hepatitis B patient with recurrent abdominal fullness, abdominal pain and general weakness for about one week. The following are the diagnoses of the patient before and after the treatment with the herbal composition of the present invention (Table 13).

TABLE 12

Diagnoses of the Patient #3 Before and After the Treatment With the YGK Herbal composition

| | TBIL (nmol/L) | ALT (U/L) | HBsAg | HbsAb | HBeAg | HbeAb | HBcAg | HBcAb (IgM) | PCR HBV-DNA |
|---|---|---|---|---|---|---|---|---|---|
| Before Treatment | 154 | 520 | + (1:64) | − | + | − | + | + | +++ |
| After Treatment | 22.1 | 29.1 | + (1:32) | − | − | + | + | − | + |

TABLE 13

Diagnoses of the Patient #4 Before and After the Treatment With the YGK Herbal composition

| | TBIL (nmol/L) | ALT (U/L) | HBsAg | HbsAb | HBeAg | HbeAb | HBcAg | HBcAb (IgM) | PCR HBV-DNA |
|---|---|---|---|---|---|---|---|---|---|
| Before Treatment | 143 | 966 | + (1:64) | + | + | − | + | + | ++ |
| After Treatment | 15.3 | 42.1 | + (1:32) | − | − | + | + | − | −− |

Table 13 shows that the patient is in a state of alleviated infection symptoms towards HBV as shown by the significant decrease of viral DNA, and viral proteins. The data also show an increase in immunity as evidenced by reduced amount of HBsAg, HBeAg, HBcAg, and an increased amount of the antibodies against the viral proteins in the serum.

Case #5 was a thirty-one years old male acute biliary hepatitis B patient with abdominal fullness and general weakness for about five (5) days and then admitted. The following are the diagnoses of the patient before and after the treatment with the herbal composition of the present invention (Table 14).

TABLE 14

Diagnoses of the Patient #5 Before and After Treatment With the YGK Herbal composition

| | TBIL (nmol/L) | ALT (U/L) | HBsAg | HbsAb | HBeAg | HbeAb | HBcAg | HBcAb (IgM) | PCR HBV-DNA |
|---|---|---|---|---|---|---|---|---|---|
| Before Treatment | 47.7 | 694 | + (1:64) | + | + | − | + | + | ++ |
| After Treatment | 19.8 | 138 | + (1:32) | + | + | − | + | − | − |

Table 14 shows that the patient is in a state of alleviated infection symptoms towards HBV as shown by the significant decrease of viral DNA, and viral proteins. The data also show an increase in immunity as evidenced by reduced amount of HBsAg, HBeAg, HBcAg, and an increased amount of the antibodies against the viral proteins in the serum.

Table 15 shows the percentage of patients with therapeutic effects in different markers.

TABLE 15

Therapeutic Effects on Patients After Treatment with the YGK Herbal composition

| Therapeutic Effects | Percentage of Patients* |
|---|---|
| Obvious therapeutic effects | 80.9% |
| Improved therapeutic effects | 19.10% |
| Hepatomegaly | 75% |
| Splenomegaly | 62.5% |
| Normalization of liver function | |
| ALT | 93.7% |
| Bilirubin | 91.1% |
| Seroconversion | |
| HBsAg(+) to HbsAg(−) | 33.3% |
| HBsAb(−) to HbsAb(+) | 23.8% |

TABLE 15-continued

Therapeutic Effects on Patients After Treatment with the YGK Herbal composition

| Therapeutic Effects | Percentage of Patients* |
|---|---|
| HbeAg(+) to HbeAg(−) | 68.6% |
| HbeAb(−) to HBeAb(+) | 23.9% |
| HBcAb(+) to HbsAb(−) | 43% |
| HBV-DNA(+) to HBV-DNA(−) | 39.5% |

*The study included a total number of 42 patients (male: 31; female: 11), who were aged between 16 and 63 (average age: 42). Before treatment, twenty six (26) of the patients were diagnosed with acute hepatitis B, eight (8) with chronic hepatitis B; and eight (8) with chronic active hepatitis B. Thirty eight (38) patients had abnormal serum ALT. Thirty four (34) patients had abnormal serum BIL. Forty two (42) patients had HBV Marker (positive+).Thirty eight (38) patients had HBV-DNA as tested by PCR (positive+). Thirty five (35) patients were HBeAg positive. Thirty two (32) patients were anti-HAV, anti-HCV, anti-HEV.

Results

The patients after being treated with the YGK herbal composition showed improvement of subjective symptoms, especially pain on liver area, fast normalization of liver function. Their ALT levels started to fall in about sixteen (16) days generally. Possible anti-viral activity was shown in the patients: the rate of HBeAg turning negative was commonly found in the YGK herbal composition treated patients (68.6%). No side-effects were noted in the treated patients.

EXAMPLE 5

Effects of the YGK Herbal Composition On Animals With Liver Diseases

The animal study was conducted at Korean Central Research Center.

Experiment 5.1

Analysis of Effect on Alcoholic or Fatty Liver in White Rats

Purpose

The experiment was conducted to investigate effects of the herbal composition on alcohol metabolism in white rats, especially, the influence on the ability to transform alcohol to triglyceride and cholesterol. The experimental dosage was 1 g/kg.

Method

The experimental animal used was male SD white rat with weight of 200 g. Blood sampling of the experimental animal was taken through orbital vein plexus. The animal was administered for the herbal composition of the present invention three (3) times a day for seven (7) days.

The experimental animals were divided into the control group and the study group. The control group animals were administered alcohol for one week. The study group animanls were administered alcohol and concomitantly with 1 g/kg of the YGK herbal composition for one week. The rats' livers were tested for triglyceride and cholesterol level, lipid hyperoxidation, and glutathione peptide.

Results

After one (1) week of alcohol administration, triglyceride and cholesterol levels in the rats' liver were increased; lipid hyperoxidation and diminished glutathione peptide occurred in the control group. In contrast, in the study group, the fatty metamorphosis of the liver was inhibited. Also, the processes of lipid hyperoxidation and diminished glutathione peptide were inhibited in the study group animals.

Conclusion

The YGH herbal composition prevents accumulation of triglyceride and cholesterol levels in the liver which follows alcohol consumption, thus providing beneficiary effects on the liver functions.

Experiment 5.2

Analysis of Effect on Liver Cirrhosis in White Rats

Purpose

The experiment was conducted to investigate the effect of the YGK herbal compositions on protein synthesis in white rats with liver cirrhosis.

Method

The experimental animal used was male SD white rat with weight of 200 g. Blood sampling of the experimental animal was taken through orbital vein plexus. The animal was administered for the herbal composition of the present invention three (3) times a day for seven (7) days.

1. Induction of Liver Cirrhosis in the Rats

The rats were injected subcutaneously on the back with 1 ml/200 g 50% chloroform ($CCl_4$) diluted in olive oil, for three (3) times a week for four (4) weeks. Liver biopsy was conducted through midline laparotomy. Most animals needed six (6) weeks of injection to induce liver cirrhosis. The injection dosage was adjusted each week in accordance to the weight of the rats.

Due to liver cirrhosis and partial liver resection, the serum alanine aminotransferase (ALT) and serum aspartate aminotransferase (AST) significantly increased in the rats.

2. Treating Rats with the YGK Herbal Composition

The rats in the study group were subdivided into three (3) groups which were respectively administered the YGK herbal composition of the present invention for 500 mg/kg, 1000 mg/kg, or 2000 mg/kg.

Results

1. ALT and AST Levels: after the treatment with the YGK herbal composition, the serum ALT and AST levels decreased in all three (3) different dosage treatment groups. The liver cirrhosis process was inhibited.

2. Hepatocyte Regeneration: after the administration of the herbal composition in three (3) different doses, the rates of liver regeneration in the rats were 19%, 30%, and 47%, respectively, higher than the rats with liver cirrhosis and partially resected livers which were not treated with the herbal composition, and the rates of liver regeneration in the treated rats were also 51%, 70%, and 92%, respectively, higher than the partially liver resected rats with normal liver functions.

Conclusion

The YGK herbal composition was effective in liver regeneration and had effectively inhibited the liver cirrhosis process.

EXAMPLE 6

Toxicity Study of the YGK Herbal Composition in Animals

Purpose

The following experiment was conducted at the Toxicology Laboratory of the Institute of Labor, Health, and Occupational Disease of Heilungkiang Province in China to examine acute toxicity of the YGK herbal composition during intravenous injection in animals.

Methods

Experimental animals were Japanese big-ear white rabbits obtained from the Animal Center of Haerbin Medical University in Haerbin, Heilungkiang Province, China. These rabbits were characterized by the obvious blood vessels on ears which facilitates the operation of injection during the experiments.

Ten (10) rabbits were obtained including six (6) males and four (4) females, each weighing between 1900 g to 3000 g.

The rabbits were randomly divided into two (2) groups, five rabbits in each group including two (2) females and three (3) males. The YGK herbal composition was intravenously injected into the rabbits through the veins on their ears at dosages of 10 g/kg and 15 g/kg, respectively, for two groups.

The concentration of injection fluid containing the herbal composition was about 1 g/ml. So the higher dosage group at 15 g/kg has a concentration of about 15 ml/kg, which could be calibrated as a sixty (60) kg-weighted adult who was treated by 900 ml of the herbal composition at a time.

The rabbits were observed for behaviour continuously for a period of two (2) weeks after intravenous injections. observation was conducted hourly at day 1; during the following days, observation was conducted four-six (4–6) times per day.

At the end of the observation period, rabbits were sacrificed and dissected to examine the eyes, liver, lung, and spleen for adverse effects.

Results

No abnormal behavior was observed of the rabbits during the observation period. The rabbits showed normal body weight increase during the period. After the sacrifice and dissection, inspection of the eyes, liver, lung, and spleen showed no extraordinary syndromes. The results when compared to a general acute toxicity index were normal and no acute toxicity.

EXAMPLE 7

Effects of the YGK Herbal Composition on HIV in Cell Cultures

Purpose

The following experiment was conducted in the Military Medical Research Institute in China to examine the effectiveness of the YGK herbal composition of the present invention in the form of intravenous product against HIV.

Methods

MT4 cells were cultured in HIV-1 suspension liquid of 100 $TCID_{50}$ in a 96-hole culture plate. The culture condition was set at a temperature of 37° C. and under 5% $CO_2$. The culture time was seven (7) days.

The YGK herbal composition of the present invention were added into the wells at various concentrations. The morphology of the MT4 cells were observed by conventional methods.

Results

No pathological changes of MT4 cells were observed in wells where the YGK herbal composition was added to in adequate concentrations. The inhibition of the pathological changes of MT4 cells indicated that the YGK herbal composition had inhibitory effect on pathological changes of the cultured cells caused by HIV.

The effective concentration of the YGK herbal composition for inhibition of the pathological changes of MT4 cells was more than 12.5 mg/ml. To achieve a 50% of inhibition, the concentration of the YGK herbal composition was 25 mg/ml.

Conclusion

The YGK herbal composition was effective in inhibiting pathological changes in cells caused by HIV-1 in vitro.

EXAMPLE 8

A Case Study on an HIV-Patient Treated With the YGK herbal Composition

Purpose

The following clinical trial was conducted in the Infectious Disease Hospital in Shanghai, China to test the effectiveness of the herbal composition of the present invention in treating an HIV-infected patient.

Methods

A fifty-year Chinese male patient diagnosed with HIV infection complicated by herpes zoster was treated with anti-virus regimens by the combination of western medicine and the herbal composition of the present invention during hospital stay.

Results

The patient was confirmed of HIV-infection by Rapid Agglutinin Assay. At the time of the initial diagnosis in August 1996, the patient showed no symptoms. Starting Jun. 1, 1997, the patient quickly developed an herpetiform rash over the front of the left side of the check extending over the nick, the shoulder, and the upper left arm. The patient was then admitted into the Hospital in Jun. 24, 1997.

At the hospital, the result of the physical examination was normal except the skin rash. The pathology tests confirmed normal renal function. The functional tests of the liver showed a slightly increased levels of serum γ glutamyl transpeptidase and acetyl glucuronidase. Hepatitis viral tests showed negative for Hepatitis B virus and Hepatitis C virus (HBV-DNA and HCV-RNA). However, Hepatitis G viral test showed positive for HGV-RNA. The immunological studies showed that the β-2 microglobulin level was 2.4–2.5 mg/ml.

During the hospital stay, haemoglobin and erythrocytes levels of the patient were slightly decreased, while the levels of the leukocyte and platelet were normal. Peripheral blood lymphocytes counts showed that T4 cells were decreased to 2.76×10/L (32.9%) and the ratio of T4/T8 cell was 1.16. Thus, the diagnosis is that the patient was with HIV infection complicated by herpes zoster.

During hospital stay, the patient had diarrhea and dry cough for a few days and was cured. In September, 1997, the patient showed HIV antibody positive by ELISA, and his T4 cells further decreased to 25.4% and the ratio of T4/T8 cells was inverted to 0.94. Then, T4 cells and the ratio of T4/T8 gradually increased after treatment with the YGK herbal composition and as tested in November 1997, his T4 cells were 40.7%, and the ratio of T4/T8 1.45. The skin rash gradually disappeared and completely recovered by the end of November.

Conclusion

The YGK herbal composition was effective in reducing symptoms of the HIV-infected patient in a treatment regime together with western medicine.

EXAMPLE 9

Clinical Trial on HIV-Infected Patients Treated with the YGK Herbal Composition Purpose The following clinical trial was conducted in De-Tang Hospital (National AIDS Therapy Center) in Beijing, China to test the effectiveness of the herbal composition of the present invention in treating HIV-infected patients.

Methods

Five (5) HIV-infected patients were treated with the YGK herbal composition. The infection was confirmed by western blotting. The profile of the patients were as follows:

| Patients | Sexuality | Age | History | Diagnosis |
|---|---|---|---|---|
| 1 | Male | 32 | 2 years | AIDS (Stage IV) |
| 2 | Female | 32 | 1 year | AIDS (Stage IV) |
| 3 | Male | 31 | 1 year | AIDS (Stage III) |
| 4 | Male | 25 | 0.5 year | AIDS (Stage II) |
| 5 | Male | 17 | 3 weeks | HIV Infection |

The patients were treated according to the following regimen:

Five (5) ml injection fluid herbal composition of the present invention was dissolved in 250 ml 5% glucose solution. The solution was injected intravenously once per day for three (3) days. Then, the dosage was increased to 15 ml injection fluid in 250 ml 5% glucose solution, and the patients were injected intravenously once per day without uncomfortable reactions for three (3) months.

Additionally, patient #1 was treated with AZT+DDI therapy for ten (10) days before being treated with the YGK herbal composition; patient #5 was treated with combination of interferon and the herbal composition.

Three (3) ml blood sample was taken from the patients each time before, during, and after the treatment and further tested for HIV.

Results
The HIV counts of the patients are as follows:

| Patients | before treatment | 1st month during treatment | 2nd month during treatment | 3rd month, at the end of treatment |
|---|---|---|---|---|
| 1 | $1.9 \times 10^4$ | $1.7 \times 10^5$ | $6.3 \times 10^3$ | $1.5 \times 10^4$ |
| 2 | $1.5 \times 10^4$ | $6.3 \times 10^3$ | | $3.8 \times 10^2$ |
| 3 | $7.3 \times 10^3$ | | $3.2 \times 10^3$ | |
| 4 | $3.0 \times 10^5$ | $1.9 \times 10^4$ | | $1.9 \times 10^4$ |
| 5 | $3.9 \times 10^5$ | $2.6 \times 10^3$ | $1.8 \times 10^3$ | * |

Note: the control level of HIV is 3,000.

Based on the above table, all patients showed decreased HIV level and increased CD4 cells, except in patient #5 who was also treated with interferon. Especially, patient #2 had significant decrease of HIV; his CD4 counts also dropped from $285/mm^3$ to $510/mm^3$.

Conclusion

The herbal composition of the present invention is effective in reducing HIV in serum in HIV-infected patients.

EXAMPLE 10

Clinical Trial on HIV-Infected Patients Treated with the YGK Herbal Composition In Russia Purpose The following experiment was conducted in Hospital in Siberia, Russia to amine the effectiveness of the YGK herbal composition of the present invention against HIV.

Methods

Five (5) HIV-infected patients were treated with the YGK herbal composition. The profile of the patients were as follows:

| Patients | Sexuality | Age | History | Diagnosis |
|---|---|---|---|---|
| 1 | Female | 23 | 2 years | AIDS (Phase A3), adenitis, hepatitis C, Syphilis, Citomegalo infection, Gonorrhea |
| 2 | Female | 28 | 2 year | AIDS (Phase A3), adenitis, hepatitis B and C, Gerpec and Citomegalo infection, Gonorrhea, drug abuse |
| 3 | Male | 35 | 1 year | AIDS (Phase B2), adenitis |
| 4 | Male | 22 | 1 year | AIDS (Phase B2), adenitis, hepatitis C, drug abuse |
| 5 | Male | 34 | several months | AIDS (phase A3), adenitis, hepatitis B and C, 10% weight loss, drug abuse |

2. The patients were treated with the herbal composition of the present invention.

Samples were taken from the patients each time before, during, and after the treatment and further tested for CD4 cells.

Results

The CD4 cells counts of the patients are as follows:

| Patients | before treatment | 2nd month during treatment | 5th month, at the end of treatment |
|---|---|---|---|
| 1 | 477 | 641 | 849 |
| 2 | 740 | 1140 | 705 |
| 3 | 421 | ... | 527 |
| 4 | 440 | 490 | 669 |
| 5 | 625 | ... | 814 |

Note: the normal level of CD4 cell count is about 500.

During the treatment process, all patients had positive response except some minor side effects. The symptoms of the patients were improved after one month of treatment including alleviation of weakness, depression, and stegnosis. The abdominal region pain and uncomfortable feeling also disappeared. Patients #4 and #5 had 5 kg increase of body weight after three (3) months of treatment. Patients #2 and #4 were disintoxicated. The biological marker of the liver showed normal after all patients after the treatment.

Based on the above table, all patients showed increased CD4 cell counts except patient #2.

Conclusion

The herbal composition of the present invention is effective in reducing symptoms in AIDS patients.

I claim:

1. An herbal pharmaceutical composition for treating patients with liver disease and/or HIV comprising a mixture of:

an entire plant of *Herba Hedyotidis diffusae* (diffuse hedyotis);

a dried rhizome of *Rhizoma Bistortae* (bistort rhizome);

a dried rhizome of *Rhizoma Polygoni Cuspidati* (giant knotweed rhizome); and a dried ripe fruit of *Fructus Schisandrae* (Chinese magnoliavine fruit);

wherein said entire plant of diffuse hedyotis, said dried rhizome of bistort rhizome, said dried rhizome of giant knotweed rhizome, and said dried ripe fruit of Chinese magnoliavine fruit are in a weight ratio of about 3:3:1:2; and wherein said mixture is extracted with water.

2. An herbal pharmaceutical composition for treating patients with liver disease and/or HIV comprising a mixture of:

an entire plant of *Herba Hedyotidis diffusae* (diffuse hedyotis);

a dried rhizome of *Rhizoma Bistortae* (bistort rhizome);

a dried rhizome of *Rhizoma Polygoni Cuspidati* (giant knotweed rhizome); and a dried ripe fruit of *Fructus Schisandrae* (Chinese magnoliavine fruit), a dried rhizome of *Rhizoma Menispermi* (Asiatic moonseed rhizome);

a dried root of *Radix Scutellariae* (baical skullcap root);

bovine biliary powder;

dried root tuber of *Radix Curcumae* (tumeric root-tuber);

a dried ripe fruit of *Fructus Crataegi* (hawthorn fruit); and a dried root of *Radix Notoginseng* (sanqi);

wherein said entire plant of diffuse hedyotis, said dried rhizome of bistort rhizome, said dried rhizome of giant knotweed rhizome, said dried ripe fruit of Chinese magnoliavine fruit, said dried rhizome of asiatic moonseed rhizome, said dried root of baical skullcap root, said bovine biliary powder, said dried root tuber of tumeric root-tuber, said dried ripe fruit of hawthorn fruit, and said dried root of sanqi are in a weight ratio of about 3:3:1:2:1:1:0.1:1:2:1; and wherein said mixture is extracted with water.

3. The herbal pharmaceutical composition according to claim 2, said mixture further comprising:

a dried ripe fruit of *Fructus Lycii* (barbary wolfberry fruit);

a steamed and dried root of *Radix Ginseng Rubra* (red ginseng);

a dried root of *Radix Scorphulariae* (figwort root);

a dried root of *Radix Angelicae sinensis* (Chinese angelica); and a dried root of *Radix Astragali* (milkvetch root);

wherein said entire plant of diffuse hedyotis, said dried rhizome of bistort rhizome, said dried rhizome of giant knotweed rhizome, said dried ripe fruit of Chinese magnoliavine fruit, said dried rhizome of asiatic moonseed rhizome, said dried root of baical skullcap root, said bovine biliary powder, said dried root tuber of tumeric root-tuber, said dried ripe fruit of hawthorn fruit, said dried root of sanqi, said dried ripe fruit of barbary wolfberry fruit, said steamed and dried root of red ginseng, said dried root of figwort root, said dried root of Chinese angelica, and said dried root of milkvetch root are in a weight ratio of about 3:3:1:2:1:1:0.1:1:2:1:3:1:2:1:3; and wherein said mixture is extracted with water.

4. The herbal pharmaceutical composition according to claim 1, wherein said liver disease comprises viral hepatitis, alcoholic or fatty liver, liver cirrhosis, and liver cancer.

5. The herbal pharmaceutical composition according to claim 4, wherein said viral hepatitis is one selected from the group consisting of hepatitis A (HAV), hepatitis B (HBV), hepatitis C (HCV), and hepatitis E (HEV).

6. A method for treating patients with liver disease comprising administering said herbal pharmaceutical composition according to claim 1 to patients with liver disease.

7. A method for treating patients with liver disease comprising administering said herbal pharmaceutical composition according to claim 2 to patients with liver disease.

8. A method for treating patients with liver disease comprising administering said herbal pharmaceutical composition according to claim 3 to patients with liver disease.

9. A method for treating patients with HIV comprising administering said herbal pharmaceutical composition according to claim 1 to patients with HIV.

10. A method for treating patients with liver disease comprising administering said herbal pharmaceutical composition according to claim 2 to patients with HIV.

11. A method for treating patients with liver disease comprising administering said herbal pharmaceutical composition according to claim 3 to patients with HIV.

12. A method for preparing the herbal pharmaceutical composition according to claim 1, comprising:

grinding and mixing the entire plant of diffuse hedyotis, the dried rhizome of bistort rhizome, the dried rhizome of giant knotweed rhizome, and the dried ripe fruit of Chinese magnoliavine fruit to form a herbal mixture;

boiling said herbal mixture in water;

filtering said boiled herbal mixture to separate said herbal mixture from a herbal solution containing herbal extracts; and concentrating said filtered herbal solution containing said herbal extracts.

13. The method according to claim 12, further comprising:

spray-drying and granulating said concentrated herbal solution to form herbal granules.

14. The method according to claim 12, wherein said herbal mixture is first boiled in water for 2 hours and then, after cooling down, is boiled again for 1.5 hours.

15. The method according to claim 12, wherein said filtered herbal solution is concentrated from about 1.4 to 1 by volume.

16. The method according to claim 13, wherein said herbal granules are encapsulated.

17. A method for preparing the pharmaceutical composition according to claim 2, comprising:

grinding and mixing the entire plant of diffuse hedyotis, the dried rhizome of bistort rhizome, the dried rhizome of giant knotweed rhizome, the dried ripe fruit of Chinese magnoliavine fruit, said asiatic moonseed rhizome, said baical skullcap root, said bovine biliary powder, said tumeric root-tuber, said hawthorn fruit, and said sanqi to form a herbal mixture;

boiling said herbal mixture in water;

filtering said boiled herbal mixture to separate said herbal mixture from a filtered herbal solution; and concentrating said filtered herbal solution containing said herbal extracts.

18. The method according to claim 17, further comprising:

spray-drying and granulating said concentrated herbal solution to form herbal granules.

19. The method according to claim 17, wherein said filtered herbal solution is concentrated from about 1.4 to 1 by volume.

20. The method according to claim 18, wherein said herbal granules are encapsulated.

21. A method for preparing the pharmaceutical composition according to claim 3, comprising:

grinding and mixing the entire plant of diffuse hedyotis, the dried rhizome of bistort rhizome, the dried rhizome of giant knotweed rhizome, the dried ripe fruit of Chinese magnoliavine fruit, said asiatic moonseed rhizome, said baical skullcap root, said bovine biliary powder, said tumeric root-tuber, said hawthorn fruit, said sanqi, said barbary wolfberry fruit, said red ginseng, saidfigwort root, Chinese angelica; and said milkvetch root to form a herbal mixture;

boiling said herbal mixture in water;

filtering said boiled herbal mixture to separate said herbal mixture from a herbal solution containing herbal extracts; and concentrating said filtered herbal solution containing herbal extracts.

22. The method according to claim 21, further comprising:

spray-drying and granulating said concentrated herbal solution to form herbal granules.

23. The method according to claim 21, wherein said filtered herbal solution is concentrated from about 1.4 to 1 by volume.

24. The method according to claim 22, wherein said herbal granules are encapsulated.

25. The herbal pharmaceutical composition according to claim 1, wherein said mixture is prepared by grinding and mixing said entire plant of diffuse hedyotis, said dried rhizome of bistort rhizome, said dried rhizome of giant knotweed rhizome, and said dried ripe fruit of Chinese magnoliavine fruit together.

26. The herbal pharmaceutical composition according to claim 2, wherein said mixture is prepared by grinding and mixing said entire plant of diffuse hedyotis, said dried rhizome of bistort rhizome, said dried rhizome of giant knotweed rhizome, and said dried ripe fruit of Chinese magnoliavine fruit, said dried rhizome of asiatic moonseed rhizome, said dried root of baical skullcap root, said bovine biliary powder, said dried root tuber of tumeric root-tuber, said dried ripe fruit of hawthorn fruit, and said dried root of sanqi together.

27. The herbal pharmaceutical composition according to claim 2, wherein said mixture is prepared by grinding and mixing said entire plant of diffuse hedyotis, said dried rhizome of bistort rhizome, said dried rhizome of giant knotweed rhizome, and said dried ripe fruit of Chinese magnoliavine fruit, said dried rhizome of asiatic moonseed rhizome, said dried root of baical skullcap root, said bovine biliary powder, said dried root tuber of tumeric root-tuber, said dried ripe fruit of hawthorn fruit, said dried root of sanqi, said dried ripe fruit of barbary wolfberry fruit, said steamed and dried root of red ginseng, said dried root of figwort root, said dried root of Chinese angelica, and said dried root of milkvetch root together.

* * * * *